United States Patent
Tsai et al.

(10) Patent No.: US 10,137,259 B2
(45) Date of Patent: *Nov. 27, 2018

(54) PORTABLE ULTRASONIC NEBULIZER AND NEBULIZATION STRUCTURE THEREOF

(71) Applicant: HCMed Innovations Co., LTD., Taipei (TW)

(72) Inventors: Wen-Yu Tsai, Taipei (TW); Chieh-Sheng Cheng, Taipei (TW)

(73) Assignee: HCMED INNOVATIONS CO., LTD., Taipei (TW)

(*) Notice: Subject to any disclaimer, the term of this patent is extended or adjusted under 35 U.S.C. 154(b) by 1012 days.

This patent is subject to a terminal disclaimer.

(21) Appl. No.: 14/532,202

(22) Filed: Nov. 4, 2014

(65) Prior Publication Data
US 2016/0022927 A1 Jan. 28, 2016

(30) Foreign Application Priority Data
Jul. 24, 2014 (TW) ............................. 103125271 A

(51) Int. Cl.
*A61M 11/00* (2006.01)
*B05B 17/00* (2006.01)
*A61M 15/00* (2006.01)

(52) U.S. Cl.
CPC ...... *A61M 11/005* (2013.01); *A61M 15/0025* (2014.02); *B05B 17/0646* (2013.01); *A61M 2209/06* (2013.01)

(58) Field of Classification Search
CPC ............ A61M 11/005; A61M 15/0025; A61M 2209/06; B05B 17/0646
See application file for complete search history.

(56) References Cited

U.S. PATENT DOCUMENTS

| | | | | |
|---|---|---|---|---|
| 5,921,237 A * | 7/1999 | Eisele | ............... | A61M 15/0045 128/203.12 |
| 2002/0002975 A1* | 1/2002 | Power | ............... | A61M 15/0085 128/203.12 |
| 2003/0150445 A1* | 8/2003 | Power | ............... | A61M 15/0085 128/200.14 |

(Continued)

*Primary Examiner* — Gregory Anderson
*Assistant Examiner* — Jonathan Paciorek
(74) *Attorney, Agent, or Firm* — Li & Cai Intellectual Property (USA) Office

(57) ABSTRACT

A nebulization structure includes a carrier unit, a vibration unit, a nebulization unit and a position-limiting unit. The carrier unit has a first carrier portion and a first surrounding portion extended from an outer perimeter of the first carrier portion, and the first carrier portion has a through hole. The vibration unit includes an annular vibrating sheet disposed on the carrier unit. The nebulization unit is disposed on the first carrier portion, and the nebulization unit has a plurality of micro holes communicated with the through hole. The position-limiting unit has a first position-limiting portion disposed on the nebulization unit and a second position-limiting portion extended from an outer perimeter of the first position-limiting portion and along the first surrounding portion. The nebulization unit is positioned between the first carrier portion and the position-limiting unit, and the first position-limiting portion has an opening for exposing the micro holes.

10 Claims, 10 Drawing Sheets

(56) References Cited

U.S. PATENT DOCUMENTS

| | | | | |
|---|---|---|---|---|
| 2003/0178024 A1* | 9/2003 | Allan | ................ | A61M 15/0045 |
| | | | | 128/200.24 |
| 2007/0221215 A1* | 9/2007 | Sugita | .................. | A61K 9/0073 |
| | | | | 128/203.12 |
| 2011/0253139 A1* | 10/2011 | Guthrie | ............... | A61M 15/009 |
| | | | | 128/203.14 |
| 2013/0126637 A1* | 5/2013 | Hsieh | ................... | A61M 11/005 |
| | | | | 239/102.2 |

* cited by examiner

PORTABLE ULTRASONIC NEBULIZER AND NEBULIZATION STRUCTURE THEREOF

BACKGROUND OF THE INVENTION

1. Field of the Invention

The instant disclosure relates to a nebulizer and a nebulization structure thereof, and more particularly to a portable ultrasonic nebulizer and a nebulization structure thereof.

2. Description of Related Art

The atomization method is often used to treat respiratory diseases. The method can be achieved by using a nebulizer, and particles sprayed by the nebulizer are droplets that are about 3~5 μm. For example, liquid medicaments can reach bronchus and lungs for therapy. The procedure typically involves aerosolized particles from liquid medicament are inhaled by the mouth and nose to enter the bronchus, and the particles then are spread to the whole alveolus so that liquid medicament can be sufficiently absorbed by the human body. This way is better than oral administration. Currently, the atomization way adapted by nebulizers usually includes pneumatic atomization, ultrasonic atomization or electronic aerosol technology (e.g., piezoelectric nozzle method) for the operating mechanism of the nebulizer.

SUMMARY OF THE INVENTION

One aspect of the instant disclosure relates to a portable ultrasonic nebulizer and a nebulization structure thereof.

One of the embodiments of the instant disclosure provides a nebulization structure, comprising: a carrier unit, a vibration unit, a waterproof package unit, a nebulization unit and a position-limiting unit. The carrier unit has a first carrier portion, a first surrounding portion extended outward from an outer perimeter of the first carrier portion, a second carrier portion extended outward from an outer perimeter of the first surrounding portion, and a second surrounding portion extended outward from an outer perimeter of the second carrier portion, wherein the first carrier portion has a through hole, and the first surrounding portion, the second carrier portion and the second surrounding portion are sequentially connected to form a surrounding groove. The vibration unit includes an annular vibrating sheet received in the surrounding groove. The waterproof package unit is received in the surrounding groove to enclose the annular vibrating sheet. The nebulization unit is disposed on the first carrier portion, wherein the nebulization unit has a plurality of micro holes communicated with the through hole. The position-limiting unit has a first position-limiting portion disposed on the nebulization unit and a second position-limiting portion extended outward from an outer perimeter of the first position-limiting portion and along the first surrounding portion, wherein the nebulization unit is positioned between the first carrier portion and the position-limiting unit, and the first position-limiting portion has an opening for exposing the micro holes.

Another one of the embodiments of the instant disclosure provides a nebulization structure, comprising: a carrier unit, a vibration unit, a nebulization unit, and a position-limiting unit. The carrier unit has a first carrier portion and a first surrounding portion extended from an outer perimeter of the first carrier portion, wherein the first carrier portion has a through hole. The vibration unit includes an annular vibrating sheet disposed on the carrier unit. The nebulization unit is disposed on the first carrier portion, wherein the nebulization unit has a plurality of micro holes communicated with the through hole. The position-limiting unit has a first position-limiting portion disposed on the nebulization unit and a second position-limiting portion extended from an outer perimeter of the first position-limiting portion and along the first surrounding portion, wherein the nebulization unit is positioned between the first carrier portion and the position-limiting unit, and the first position-limiting portion has an opening for exposing the micro holes.

Yet another one of the embodiments of the instant disclosure provides a portable ultrasonic nebulizer, comprising: a casing structure and a nebulization structure. The casing structure includes an outer casing, a top cover rotatably disposed on a top side of the outer casing, and a nozzle disposed on an outer perimeter surface of the outer casing, wherein the outer casing has a receiving space formed on the top side thereof and covered by the top cover. The nebulization structure is received in the outer casing and communicated between the receiving space and the nozzle, wherein the nebulization structure comprises a carrier unit, a vibration unit, a waterproof package unit, a nebulization unit, and a position-limiting unit. The carrier unit has a first carrier portion, a first surrounding portion extended outward from an outer perimeter of the first carrier portion, a second carrier portion extended outward from an outer perimeter of the first surrounding portion, and a second surrounding portion extended outward from an outer perimeter of the second carrier portion, wherein the first carrier portion has a through hole. The first surrounding portion, the second carrier portion, and the second surrounding portion are sequentially connected to form a surrounding groove. The vibration unit includes an annular vibrating sheet received in the surrounding groove. The waterproof package unit is received in the surrounding groove to enclose the annular vibrating sheet. The nebulization unit is disposed on the first carrier portion, wherein the nebulization unit has a plurality of micro holes communicated with the through hole. The position-limiting unit has a first position-limiting portion disposed on the nebulization unit and a second position-limiting portion extended outward from an outer perimeter of the first position-limiting portion and along the first surrounding portion, wherein the nebulization unit is positioned between the first carrier portion and the position-limiting unit, and the first position-limiting portion has an opening for exposing the micro holes.

More precisely, the portable ultrasonic nebulizer further comprises a medicine accommodating structure, wherein the medicine accommodating structure comprises: a medicine accommodating unit and a movable unit. The medicine accommodating unit is disposed in the receiving space, wherein the medicine accommodating unit includes a main body, at least one auxiliary portion adjacent to the main body, a medicine accommodating space surrounded by the main body and the at least one auxiliary portion and communicated with the receiving space, a first opening formed between one of two opposite ends of the main body and one of two opposite ends of the at least one auxiliary portion and communicated between the receiving space and the medicine accommodating space, and a second opening formed between the other end of the main body and the other end of the at least one auxiliary portion and communicated between the receiving space and the medicine accommodating space. The movable unit is extended from an inner surface of the top cover into the receiving space, wherein the movable unit is movably disposed between the receiving space and the medicine accommodating space through the first opening. At least one pharmaceutical capsule having a medicinal liquid received therein is placed inside the medicine accommodating space. Whereby, when the movable unit is moved from the receiving space into the medicine accommodating space, the movable unit pierces into the at least one pharmaceutical capsule, such that the medicinal liquid flows from the at least one pharmaceutical capsule into the receiving space.

Therefore, the nebulization unit can be positioned between the first carrier portion and the position-limiting unit due to the design of "the position-limiting unit has a first position-limiting portion disposed on the nebulization unit and a second position-limiting portion extended outward from an outer perimeter of the first position-limiting portion and along the first surrounding portion".

To further understand the techniques, means and effects of the instant disclosure applied for achieving the prescribed objectives, the following detailed descriptions and appended drawings are hereby referred to, such that, and through which, the purposes, features and aspects of the instant disclosure can be thoroughly and concretely appreciated. However, the appended drawings are provided solely for reference and illustration, without any intention to limit the instant disclosure.

DETAILED DESCRIPTION OF THE PREFERRED EMBODIMENTS

The embodiments of "a portable ultrasonic nebulizer and a nebulization structure thereof" of the instant disclosure are described. Other advantages and objectives of the instant disclosure can be easily understood by one skilled in the art from the disclosure. The instant disclosure can be applied in different embodiments. Various modifications and variations can be made to various details in the description for different applications without departing from the scope of the instant disclosure. The drawings of the instant disclosure are provided only for simple illustrations, but are not drawn to scale and do not reflect the actual relative dimensions. The following embodiments are provided to describe in detail the concept of the instant disclosure, and are not intended to limit the scope thereof in any way.

Figure 1:
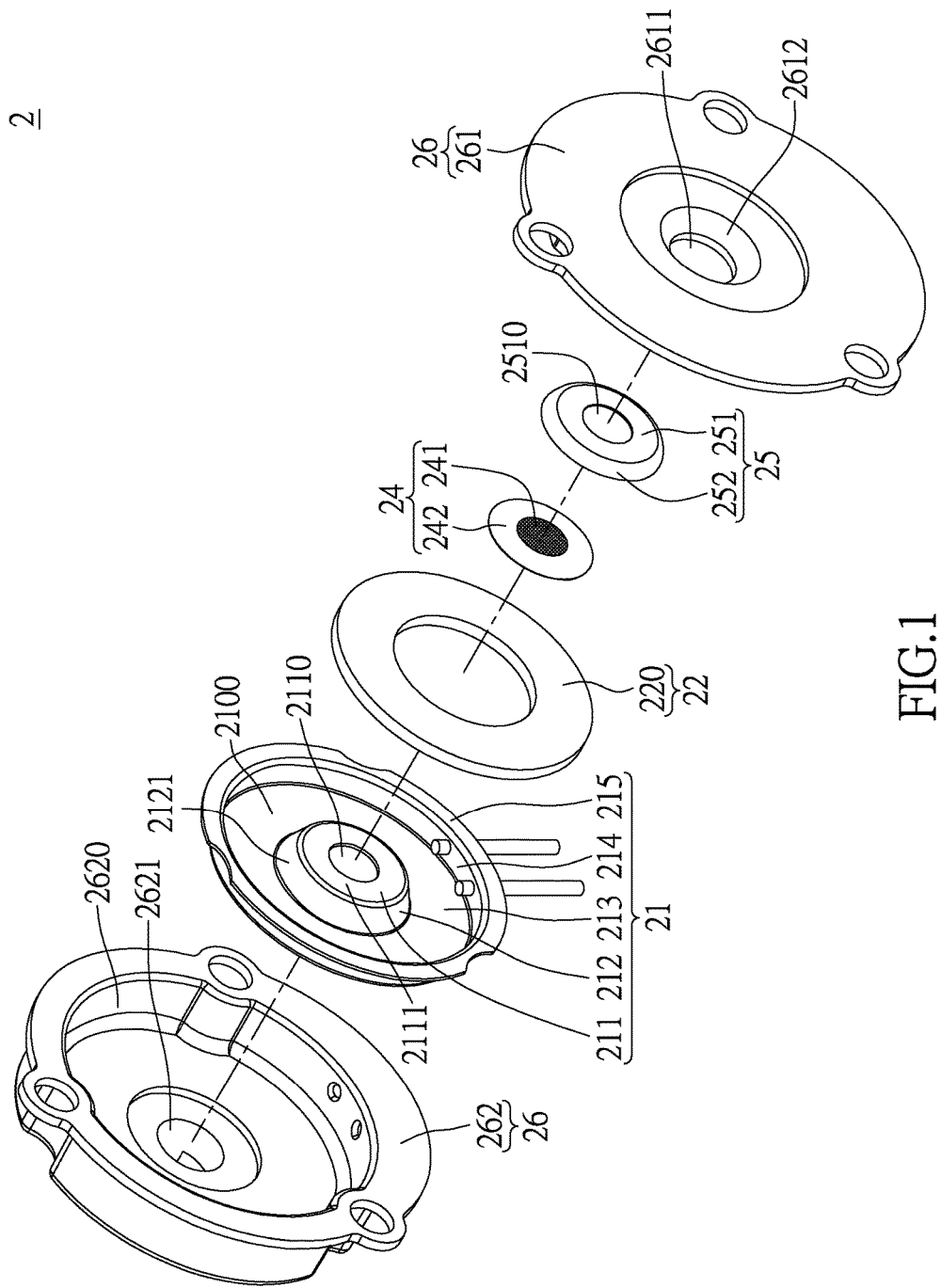
FIG. 1 shows an exploded schematic view of a nebulization structure according to the instant disclosure.
Figure 2:
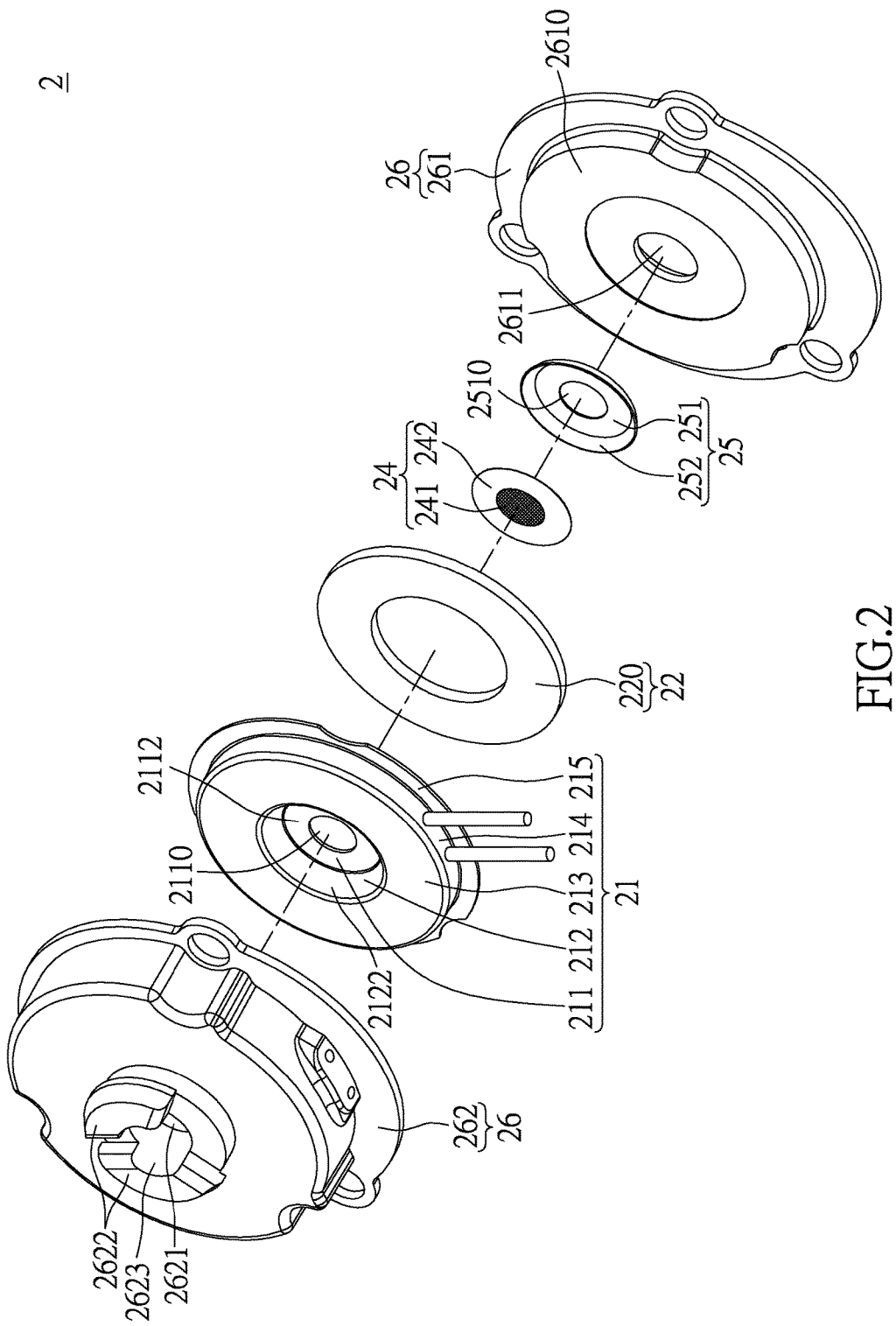
FIG. 2 shows another exploded schematic view of the nebulization structure according to the instant disclosure.
Figure 3:
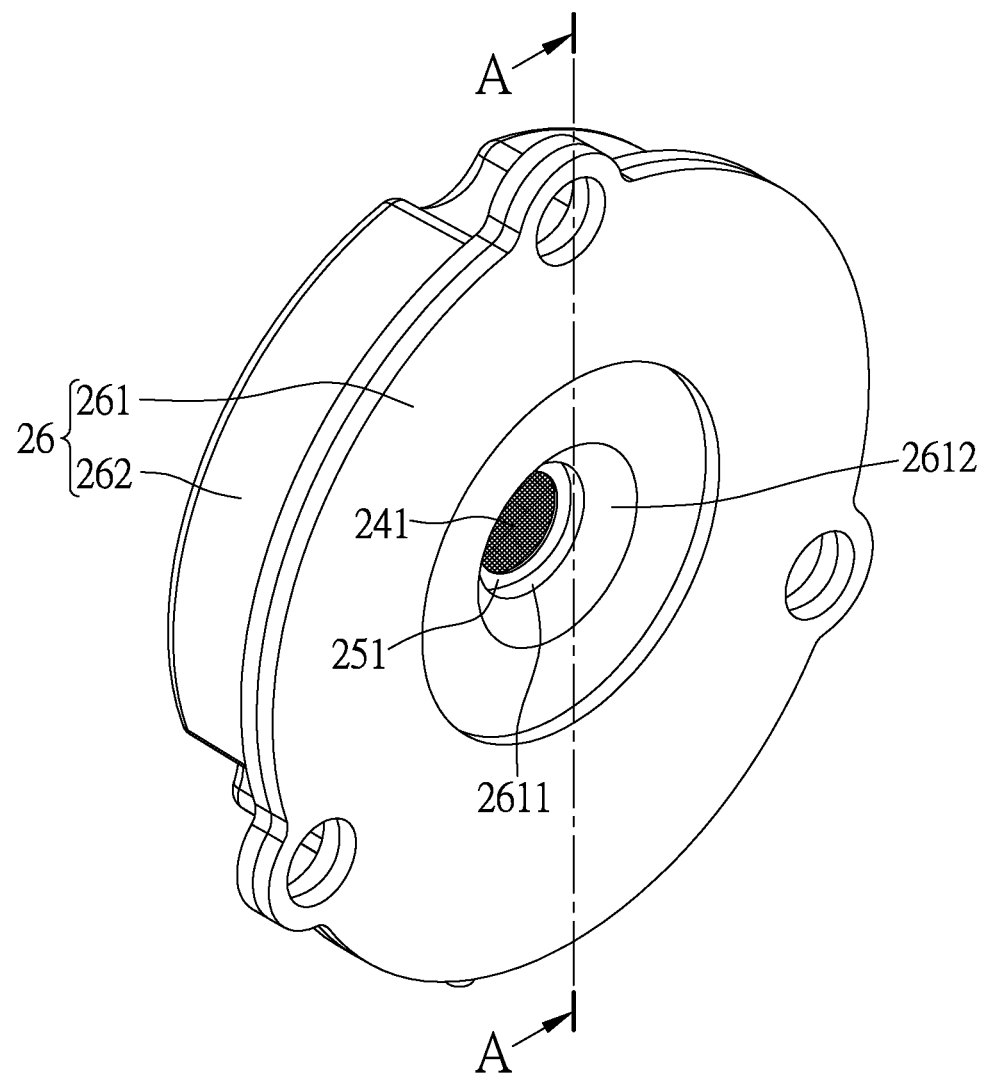
FIG. 3 shows an assembled schematic view of the nebulization structure according to the instant disclosure.

Referring to FIG. 1 to FIG. 4, FIG. 4 shows a cross-sectional view taken along the section line A-A of FIG. 3. The instant disclosure provides a nebulization structure 2, comprising: a carrier unit 21, a vibration unit 22, a waterproof package unit 23, a nebulization unit 24, and a position-limiting unit 25.

Figure 4:
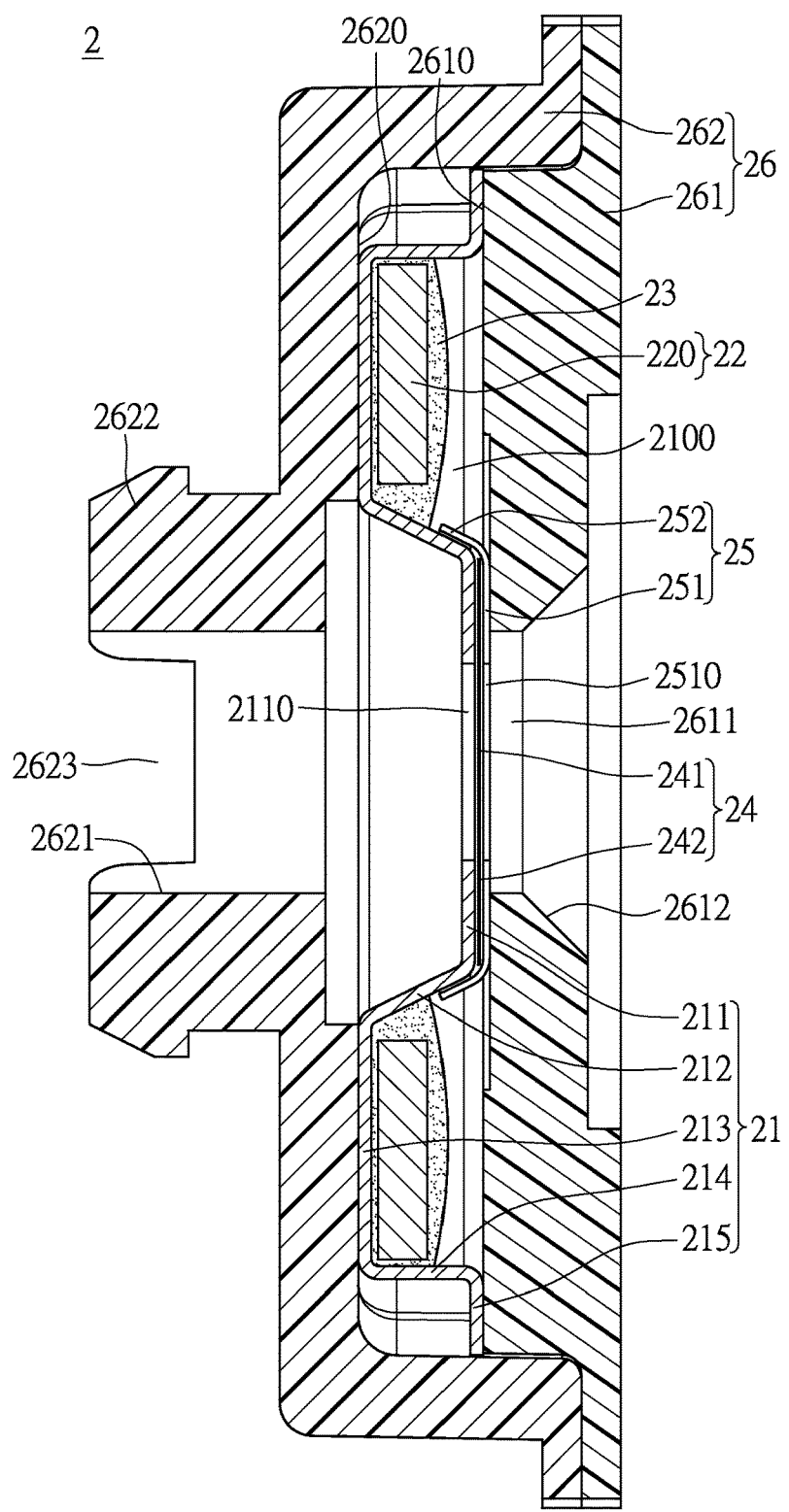
FIG. 4 shows a cross-sectional view taken along the section line A-A of FIG. 3.

Referring to FIG. 1, FIG. 2 and FIG. 4, the carrier unit 21 has a first carrier (carrying) portion 211, a first surrounding (annular) portion 212 extended outward from an outer perimeter (such as an outer surrounding periphery) of the first carrier portion 211, a second carrier portion 213 extended outward from an outer perimeter of the first surrounding portion 212, and a second surrounding portion 214 extended outward from an outer perimeter of the second carrier portion 213. The first carrier portion 211 has a through hole 2110. The first surrounding portion 212, the second carrier portion 213, and the second surrounding portion 214 are sequentially connected to form a surrounding groove 2110. More precisely, as shown in FIG. 4, the first surrounding portion 212 can be extended backward and slantwise from the outer perimeter of the first carrier portion 211. The second carrier portion 213 can be extended vertically from the outer perimeter of the first surrounding portion 212 (or extended in a direction perpendicular to the first surrounding portion 212) and horizontal (parallel) to the first carrier portion 211. The second surrounding portion 214 can be extended frontward and horizontally from the outer perimeter of the second carrier portion 213 and vertical to the second carrier portion 213. In addition, the carrier unit 21 further has a surrounding end portion 215 extended outward and horizontally from the outer perimeter of the second surrounding portion 214 and horizontal to the first carrier portion 211.

Moreover, referring to FIG. 1 and FIG. 4, the vibration unit 22 includes an annular vibrating sheet 220 disposed on the carrier unit 21 and received in the surrounding groove 2100. The waterproof package unit 23 (as shown in FIG. 4) is received in the surrounding groove 2100 to enclose the annular vibrating sheet 220. For example, the annular vibrating sheet 220 may be a piezoelectric driver made of any piezoelectric material, and the waterproof package unit 23 may be any type of package material for preventing the annular vibrating sheet 220 from being influenced by external water vapor or moisture.

Furthermore, referring to FIG. 1, FIG. 2 and FIG. 4, the nebulization unit 24 such as an atomizer plate or a nozzle sheet disposed on the first carrier portion 211, and the nebulization unit 24 has a plurality of micro holes (or micro nozzles) 241 communicated with (in fluid communication with) the through hole 2110. In addition, the position-limiting unit 25 has a first position-limiting portion 251 disposed on the nebulization unit 24 and a second position-limiting portion 252 extended outward from the outer perimeter of the first position-limiting portion 251 along the first surrounding portion 212. The nebulization unit 24 is positioned between the first carrier portion 211 and the position-limiting unit 25, and the first position-limiting portion 251 has an opening 2510 for exposing the micro holes 241.

More precisely, referring to FIG. 1, FIG. 2 and FIG. 4, the first carrier portion 211 has a front surface 2111 and a rear surface 2112 opposite to the front surface 2111. The first surrounding portion 212 has a first surrounding surface 2121 connected to the front surface 2111 and a second surrounding surface 2122 opposite to the first surrounding surface 2121. The second surrounding surface 2122 is connected to the rear surface 2112. In addition, the nebulization unit 24 has a surrounding positioning portion 242 disposed between the front surface 2111 of the first carrier portion 211 and the first position-limiting portion 251 for surrounding the micro holes 241. Referring to FIG. 1 and FIG. 4, the front surface 2111 of the first carrier portion 211 is totally enclosed by the surrounding positioning portion 242, and one portion of the first surrounding surface 2121 of the first surrounding portion 212 is enclosed by the second position-limiting portion 252.

More precisely, referring to FIG. 1 to FIG. 4, the nebulization structure 2 further comprises a casing unit 26. The carrier unit 21, the vibration unit 22, the waterproof package unit 23, the nebulization unit 24, and the position-limiting unit 25 are received in the casing unit 26. In addition, the casing unit 26 includes a front casing 261 and a rear casing 262 mated with the front casing 261. The front casing 261 has an outlet port 2611 for exposing the micro holes 241 and a trumpet-shaped opening 2612 in fluid communication with the outlet port 2611. The rear casing 262 has an inlet port 2621 corresponding to the outlet port 2611, a plurality of convex blocks 2622 adjacent to and surrounding the inlet port 2621, and a water-bearing space 2623 (such as a water-containing space) surrounded by the convex blocks 2622. The water-bearing space 2623 is in fluid communication with the inlet port 2621 for increasing the water content of the inlet area. Moreover, as shown in FIG. 4, the first position-limiting portion 251 of the position-limiting unit 25 and the surrounding end portion 215 can be concurrently abutted against an inner surface 2610 of the front casing 261, whereas the second carrier portion 213 can be abutted against an inner surface 2620 of the rear casing 262.

Figure 5:
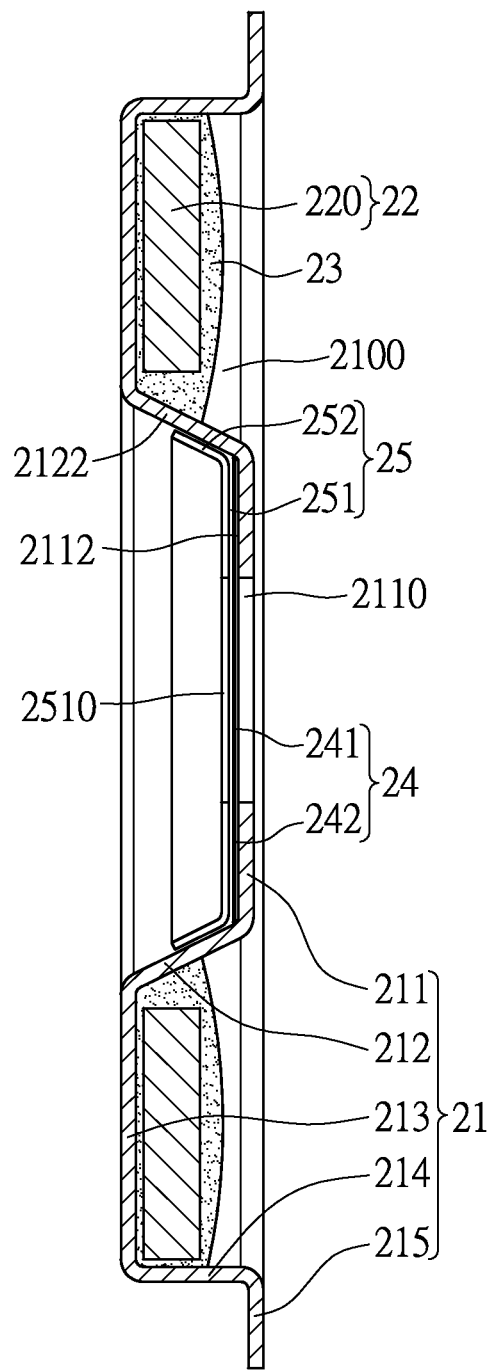
FIG. 5 shows a cross-sectional, schematic view of another nebulization structure according to the instant disclosure.

It is worth mentioning that, as shown in FIG. 5, the nebulization unit 24 has a surrounding positioning portion 242 disposed between the rear surface 2112 of the first carrier portion 211 and the first position-limiting portion 251 for surrounding the micro holes 241. The rear surface 2112 of the first carrier portion 211 can be completely enclosed by the surrounding positioning portion 242, and one portion of the second surrounding surface 2122 of the first surrounding portion 212 can be enclosed by the second position-limiting portion 252. In addition, the first carrier portion 211 and the surrounding end portion 215 can be concurrently abutted against an inner surface 2610 of the front casing 261, and the second carrier portion 213 can be abutted against an inner surface 2620 of the rear casing 262. Hence, the nebulization unit 24 and the position-limiting unit 25 can be disposed in front of the carrier unit 21 (as shown in FIG. 4), but also can be disposed behind the carrier unit 21 (as shown in FIG. 5).

Figure 6:
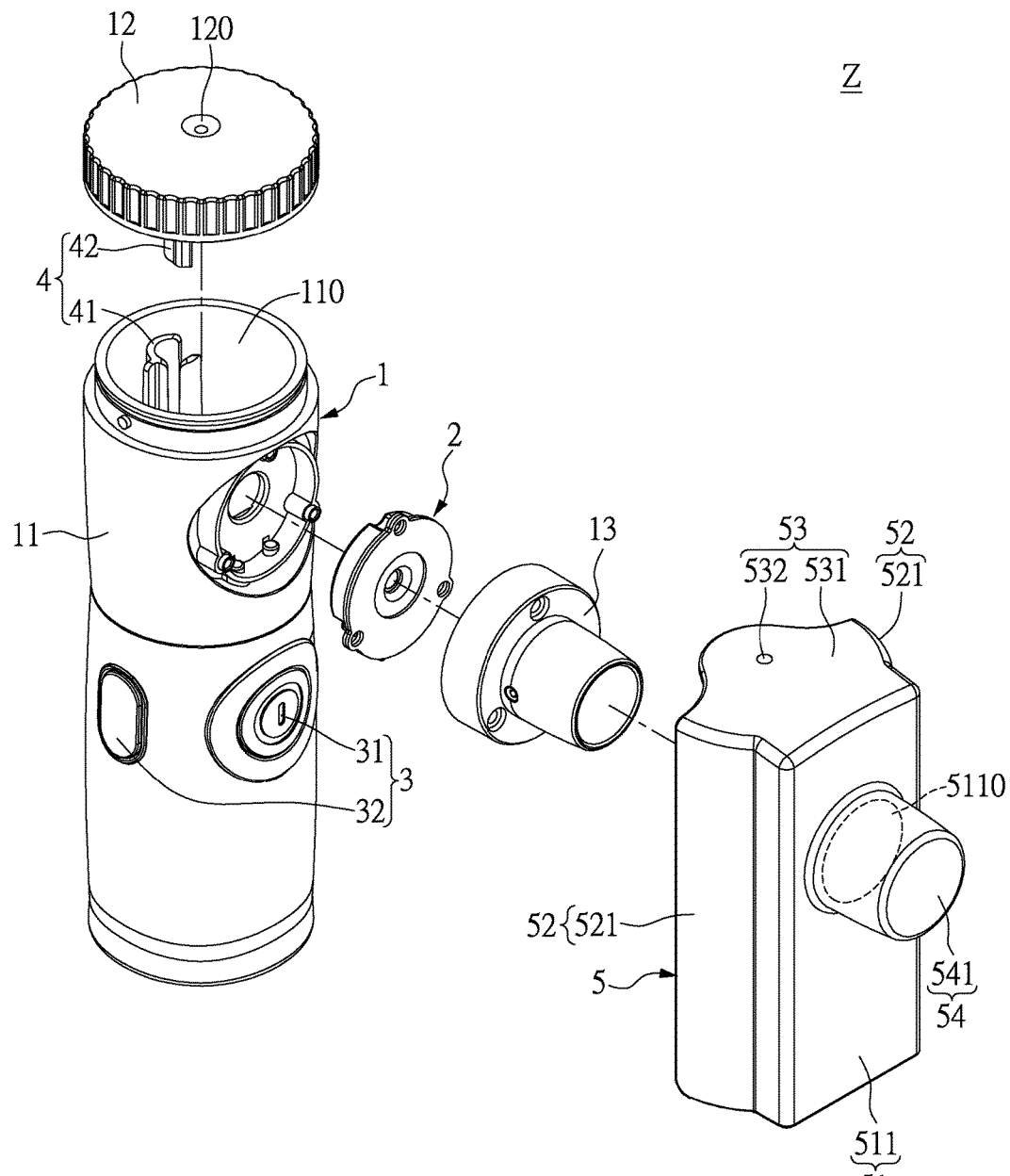
FIG. 6 shows a partially exploded schematic view of a portable ultrasonic nebulizer according to the instant disclosure.
Figure 7:
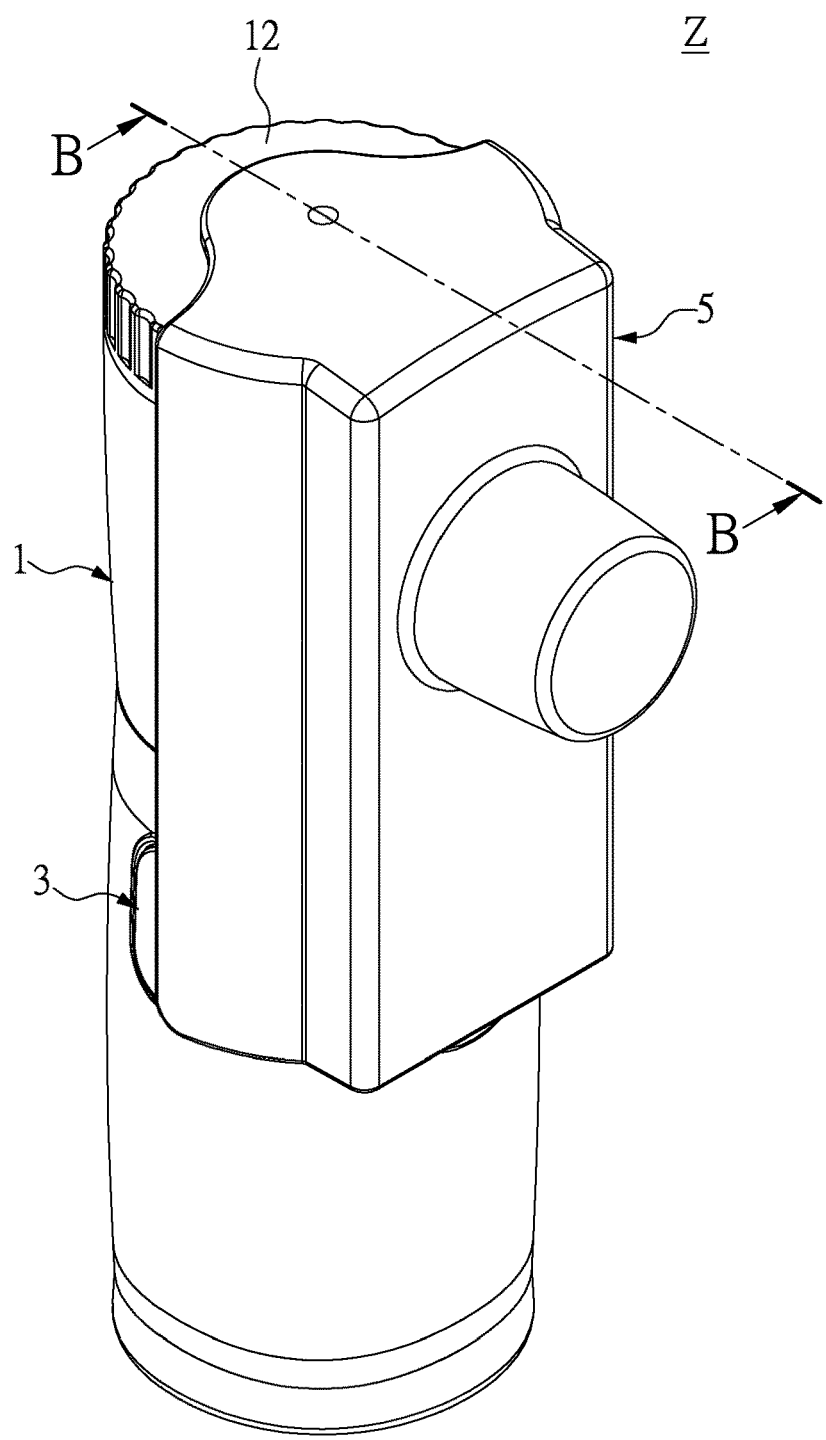
FIG. 7 shows an assembled schematic view of the portable ultrasonic nebulizer according to the instant disclosure.
Figure 8:
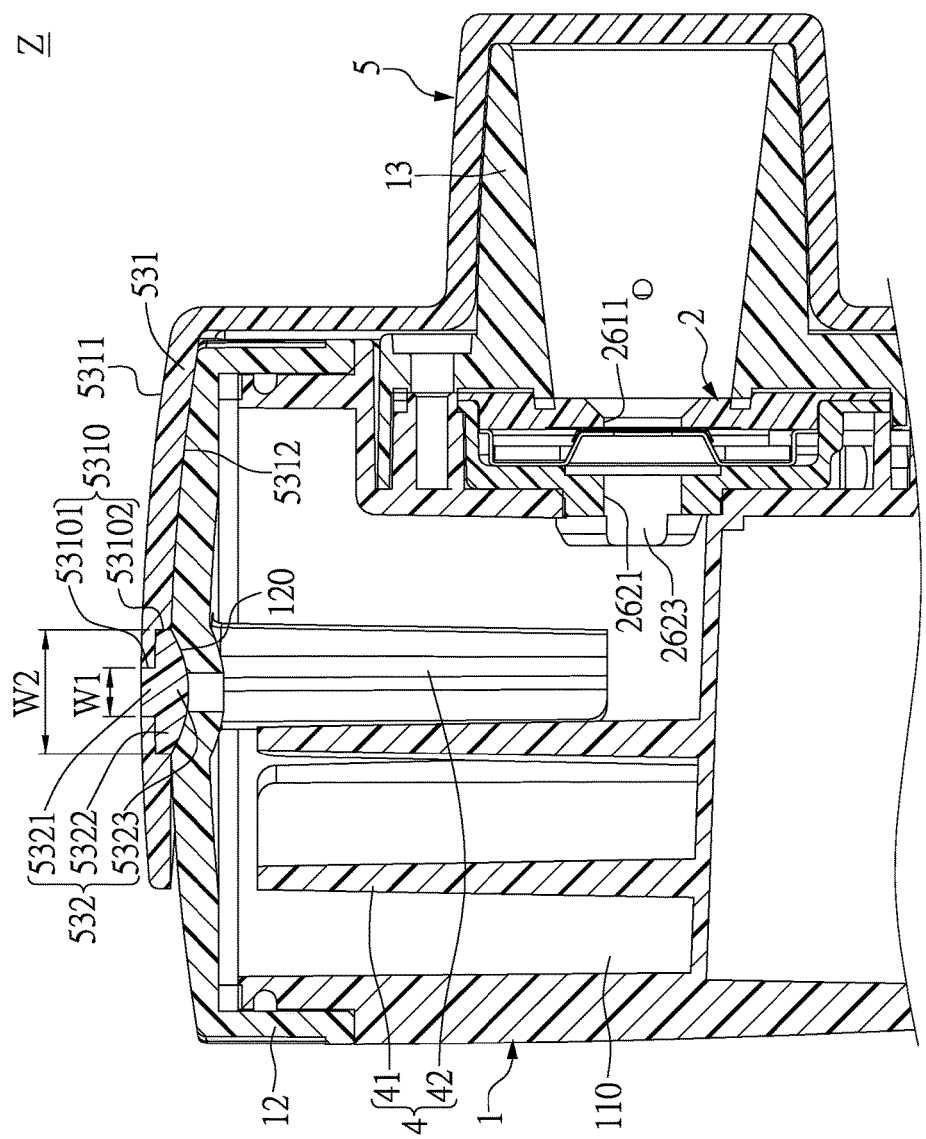
FIG. 8 shows a cross-sectional view taken along the section line B-B of FIG. 7.

Furthermore, referring to FIG. 6 to FIG. 8, the instant disclosure provides a portable ultrasonic nebulizer Z, comprising: a casing structure 1, a nebulization structure 2, and a push button structure 3. The casing structure 1 includes an outer casing 11, a top cover 12 rotatably disposed on a top side of the outer casing 11, and a nozzle 13 disposed on an outer perimeter surface of the outer casing 11. The outer casing 11 has a receiving space 110 formed on the top side thereof and the receiving space 110 is covered by the top cover 12. The top cover 12 has an exhaust vent 120 in fluid communication with the receiving space 110. In addition, the nebulization structure 2 is received in the outer casing 11 and is in fluid communication between the receiving space 110 and the nozzle 13. The push button structure 3 includes a power push button 31 disposed on the outer perimeter surface of the outer casing 11 and at least one switching push button 32 disposed on the outer perimeter surface of the outer casing 11.

More precisely, referring to FIG. 6 and FIG. 8 to FIG. 10, the portable ultrasonic nebulizer Z further comprises a medicine accommodating structure 4 (such as a cartridge structure), and the medicine accommodating structure 4 includes a medicine accommodating unit 41 and a movable unit 42.

Figure 9:
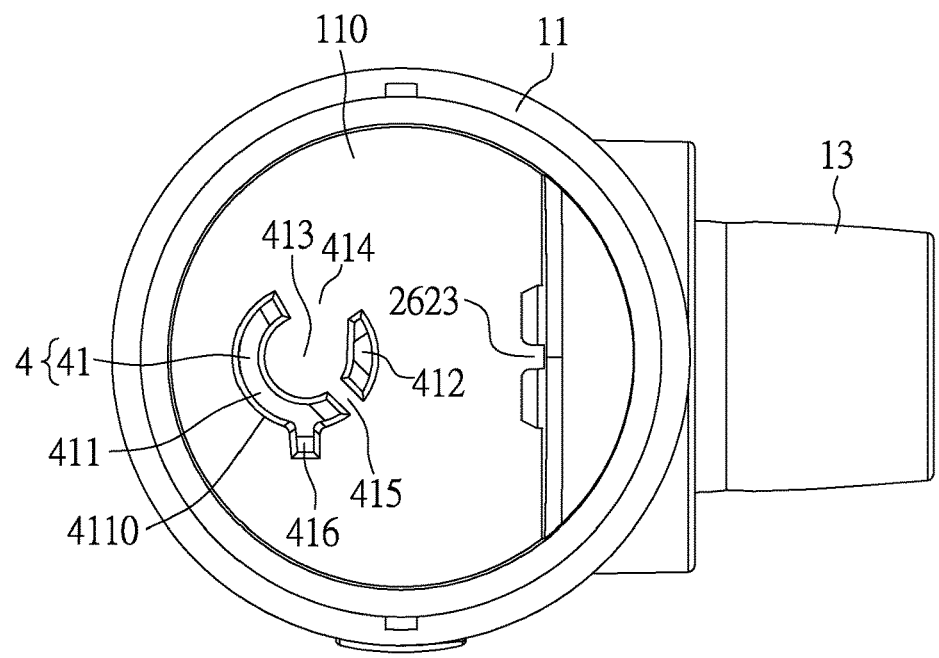
FIG. 9 shows a top schematic view of the portable ultrasonic nebulizer without a top cover according to the instant disclosure.

First, referring to FIG. 6 and FIG. 9, FIG. 8 shows a cross-sectional view taken along the section line B-B of FIG. 7. The medicine accommodating unit 41 is disposed in the receiving space 110. For example, the medicine accommodating unit 41 includes a main body 411, at least one auxiliary portion 412 adjacent to the main body 411, a medicine accommodating space 413 (such as a cartridge accommodation space) surrounded by the main body 411 and the at least one auxiliary portion 412, a first opening 414 formed between one of two opposite ends of the main body 411 and one of two opposite ends of the at least one auxiliary portion 412, a second opening 415 formed between the other end of the main body 411 and the other end of the at least one auxiliary portion 412, and a reinforcement rib 416 connected (or integrally connected) to an outer surface 4110 of the main body 411. The medicine accommodating space 413 is in fluid communication with the receiving space 110, the first opening 414 is in fluid communication between the receiving space 110 and the medicine accommodating space 413, and the second opening 415 is in fluid communication between the receiving space 110 and the medicine accommodating space 413.

Figure 10:
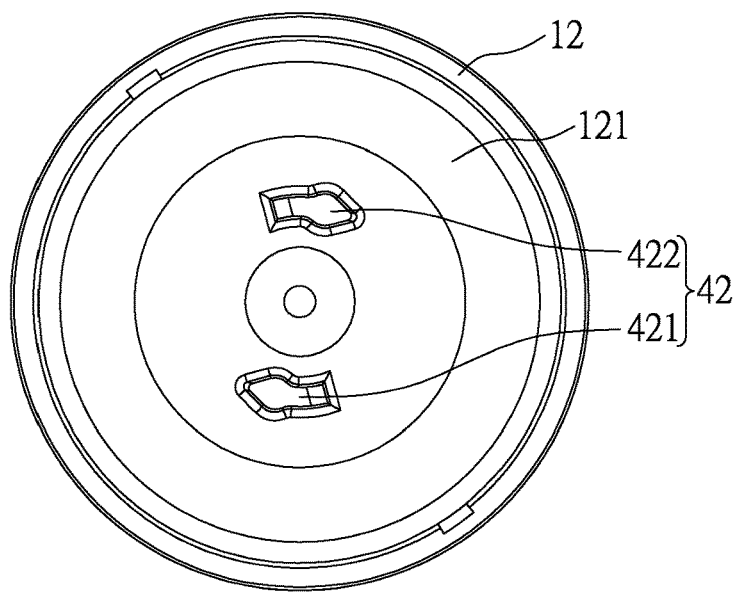
FIG. 10 shows a bottom schematic view of the top cover according to the instant disclosure.

Moreover, referring to FIG. 6, FIG. 8 and FIG. 10, the movable unit 42 is extended from an inner surface 121 of the top cover 12 into the receiving space 110. For example, the movable unit 42 includes a first movable element 421 extended from the inner surface 121 of the top cover 12 into the receiving space 110 and a second movable element 422 extended from the inner surface 121 of the top cover 12 into the receiving space 110. The first movable element 421 and the second movable element 422 can be symmetrically disposed on the inner surface 121 of the top cover 12.

Figure 11:
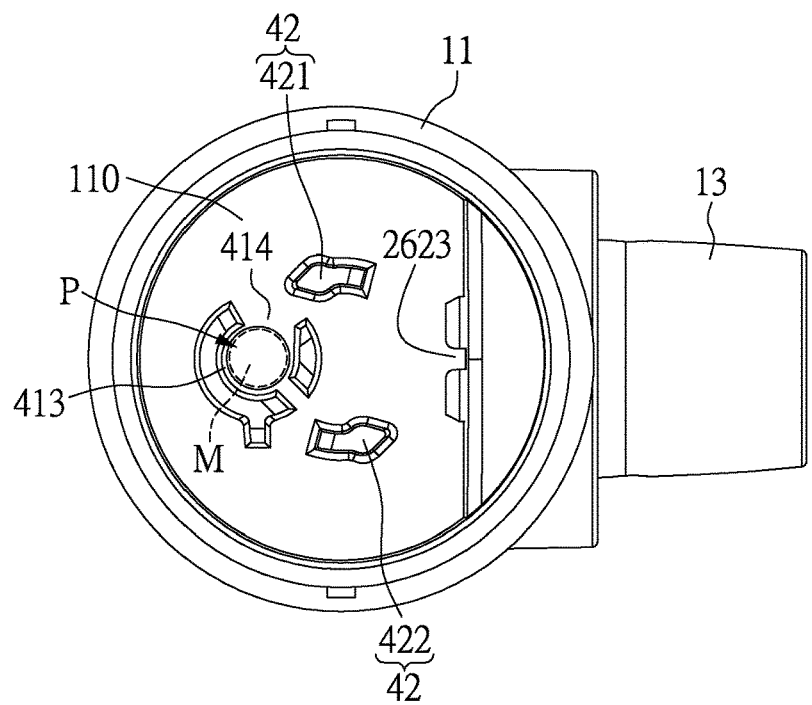
FIG. 11 shows a top schematic view demonstrating a pharmaceutical capsule before a movable unit is piercing into according to the instant disclosure.
Figure 12:
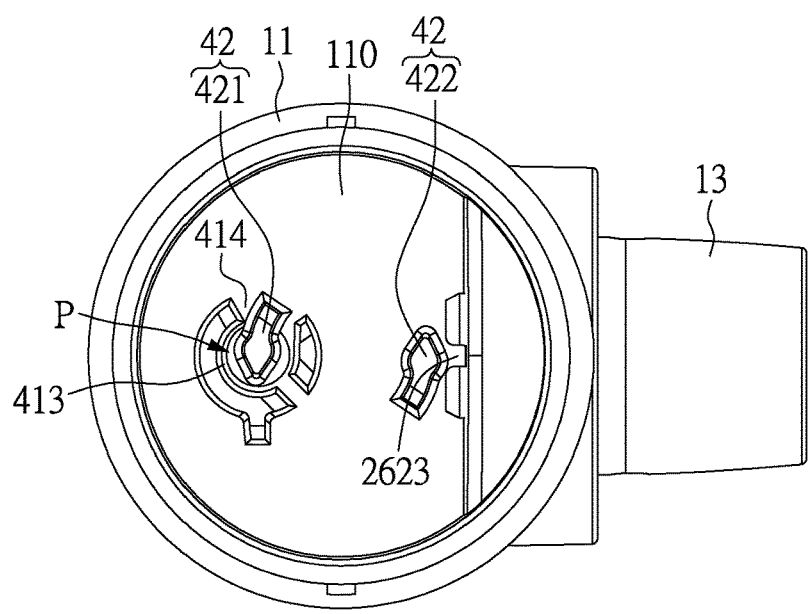
FIG. 12 shows a top schematic view demonstrating a pharmaceutical capsule after a movable unit is piercing into according to the instant disclosure.

More precisely, referring to FIG. 11 and FIG. 12, the movable unit 42 is movably disposed between the receiving space 110 and the medicine accommodating space 413 through the first opening 414. In other words, when the top cover 12 is rotated counterclockwise by the user to concurrently move the first movable element 421 and the second movable element 422, one of the two movable elements, the first movable element 421 and the second movable element 422, can be moved between the receiving space 110 and the medicine accommodating space 413 through the first opening 414. More precisely, when the top cover 12 is rotated counterclockwise by the user to concurrently move the first movable element 421 and the second movable element 422, one of the two movable elements, the first movable element 421 and the second movable element 422, can pass through the first opening 414 and move from the receiving space 110 into the medicine accommodating space 413 or from the medicine accommodating space 413 to the receiving space 110. For example, at least one pharmaceutical capsule P has a medicinal liquid M received therein and the pharmaceutical capsule P is placed inside the medicine accommodating space 413. When the movable unit 42 is moved from the receiving space 110 into the medicine accommodating space 413, the movable unit 42 can pierce into the at least one pharmaceutical capsule P, such that the medicinal liquid M can flow from the at least one pharmaceutical capsule P into the receiving space 110. When the medicinal liquid M flows into the water-bearing space 2623, the medicinal liquid M can be nebulized by the nebulization structure 2.

Furthermore, referring to FIG. 6 to FIG. 8, the portable ultrasonic nebulizer Z further comprises a protection structure 5. The protection structure 5 is disposed on the casing structure 1 for protecting the portable ultrasonic nebulizer Z. The protection structure 5 includes a first protection unit 51, a second protection unit 52, a third protection unit 53, and a fourth protection unit 54.

First, referring to FIG. 6 and FIG. 7, the first protection unit 51 includes a first protection body 511 having a via hole 5110, and the first protection body 511 is disposed in front of the power push button 31 for covering the power push button 31. The second protection unit 52 includes two second protection bodies 521 corresponding to each other. The two second protection bodies 521 are respectively extended backward from two opposite sides of the first protection body 511, and one of the two second protection bodies 521 is disposed in front of the at least one switching push button 32 for covering the at least one switching push button 32. The third protection unit 53 includes a third protection body 531 extended backward from a top side of the first protection body 511 and connected between the two second protection bodies 521 and an elastic body 532 connected with the third protection body 531. The third protection body 53 is disposed on the top cover 12. One portion of the elastic body 532 is received in the exhaust vent 120 of the top cover 12 for enclosing the exhaust vent 120 of the top cover 12. The fourth protection unit 54 includes a fourth protection body 541 extended forward from a front side of the first protection body 511. The nozzle 13 is covered by the fourth protection body 541 for protecting the nebulization structure 2. In other words, the protection structure 5 includes a plurality of protection units. One of the protection units (such as the fourth protection unit 54) has a protection body (such as the fourth protection body 541) and an elastic body 532 connected with the protection body, in which the protection body is disposed on the top cover 12, and one portion of the elastic body 532 is received inside the exhaust vent 120 of the top cover 12 for enclosing the exhaust vent 120 of the top cover 12. Thus, the protection structure 5 can prevent both the power push button 31 and the at least one switching push button 32 from being touched by any foreign body, and also can prevent the medicinal liquid M received inside the receiving space 110 from leaking out of the exhaust vent 120 of the top cover 12.

More precisely, referring to FIG. 7 and FIG. 8, the third protection body 531 has a receiving hole 5310. The receiving hole 5310 has a first receiving portion 53101 connected to an outer surface 5311 of the third protection body 531 and a second receiving portion 53102 connected to an inner surface 5312 of the third protection body 531. The second receiving portion 53102 is in fluid communication with the first receiving portion 53101. The width W2 of the second receiving portion 53102 is larger than the width W1 of the first receiving portion 53101. The elastic body 532 has a first elastic portion 5321 received in the first receiving portion 53101, a second elastic portion 5322 connected with the first elastic portion 5321, and a third elastic portion 5323 extended downward from the second elastic portion 5322. The second elastic portion 5322 is received in the second receiving portion 53102, and third elastic portion 5323 is received in the exhaust vent 120 of the top cover 12.

In conclusion, the nebulization unit 24 can be positioned between the first carrier portion 211 and the position-limiting unit 25 due to the design of "the position-limiting unit 25 has a first position-limiting portion 251 disposed on the nebulization unit 24 and a second position-limiting portion 252 extended outward from an outer perimeter of the first position-limiting portion 251 along the first surrounding portion 212".

The aforementioned descriptions merely represent the preferred embodiments of the instant disclosure, without any intention to limit the scope of the instant disclosure which is fully described only within the following claims. Various equivalent changes, alterations or modifications based on the claims of the instant disclosure are all, consequently, viewed as being embraced by the scope of the instant disclosure.

What is claimed is:

1. A nebulization structure, comprising:
   a carrier unit having a first carrier portion, a first surrounding portion extended outward from an outer perimeter of the first carrier portion, a second carrier portion extended outward from an outer perimeter of the first surrounding portion, and a second surrounding portion extended outward from an outer perimeter of the second carrier portion, wherein the first carrier portion has a through hole, and the first surrounding portion, the second carrier portion and the second surrounding portion are sequentially connected to form a surrounding groove, wherein the first surrounding portion is extended backward and slantwise from the outer perimeter of the first carrier portion;
   a vibration unit including an annular vibrating sheet received in the surrounding groove;
   a waterproof package unit received in the surrounding groove to enclose the annular vibrating sheet;
   a nebulization unit disposed on the first carrier portion, wherein the nebulization unit has a plurality of micro holes communicated with the through hole; and
   a position-limiting unit having a first position-limiting portion disposed on the nebulization unit and a second position-limiting portion extended outward and slantwise from an outer perimeter of the first position-limiting portion and along the first surrounding portion, wherein the nebulization unit is positioned between the first carrier portion and the position-limiting unit, and the first position-limiting portion has an opening for exposing the micro holes.

2. The nebulization structure of claim 1, further comprising a casing unit, wherein the carrier unit, the vibration unit, the waterproof package unit, the nebulization unit and the position-limiting unit are received in the casing unit, the casing unit includes a front casing and a rear casing mated with the front casing, the front casing has an outlet port and a trumpet-shaped opening communicated with the outlet port, and the rear casing has an inlet port corresponding to the outlet port, a plurality of convex blocks adjacent to the inlet port and surrounding the inlet port, and a water-bearing space surrounded by the convex blocks and communicated with the inlet port, wherein the second carrier portion is extended vertically from the outer perimeter of the first surrounding portion and horizontal to the first carrier portion, the second surrounding portion is extended frontward and horizontally from the outer perimeter of the second carrier portion and vertical to the second carrier portion, and the carrier unit has a surrounding end portion extended outward and horizontally from the outer perimeter of the second surrounding portion and horizontal to the first carrier portion, wherein the first carrier portion has a front surface and a rear surface opposite to the front surface, and the first surrounding portion has a first surrounding surface connected to the front surface and a second surrounding surface opposite to the first surrounding surface and connected to the rear surface.

3. The nebulization structure of claim 2, wherein the nebulization unit has a surrounding positioning portion disposed between the front surface of the first carrier portion and the first position-limiting portion and surrounding the micro holes, the front surface of the first carrier portion is enclosed by the surrounding positioning portion, and one portion of the first surrounding surface of the first surrounding portion is enclosed by the second position-limiting portion, wherein the position-limiting unit and the surrounding end portion are abutted against an inner surface of the front casing, and the second carrier portion is abutted against an inner surface of the rear casing.

4. The nebulization structure of claim 2, wherein the nebulization unit has a surrounding positioning portion disposed between the rear surface of the first carrier portion and the first position-limiting portion and surrounding the micro holes, the rear surface of the first carrier portion is enclosed by the surrounding positioning portion, and one portion of the second surrounding surface of the first surrounding portion is enclosed by the second position-limiting portion.

5. A nebulization structure, comprising:
a carrier unit having a first carrier portion and a first surrounding portion extended from an outer perimeter of the first carrier portion, wherein the first carrier portion has a through hole, wherein the first surrounding portion is extended backward and slantwise from the outer perimeter of the first carrier portion;
a vibration unit including an annular vibrating sheet disposed on the carrier unit;
a nebulization unit disposed on the first carrier portion, wherein the nebulization unit has a plurality of micro holes communicated with the through hole; and
a position-limiting unit having a first position-limiting portion disposed on the nebulization unit and a second position-limiting portion extended and slantwise from an outer perimeter of the first position-limiting portion and along the first surrounding portion, wherein the nebulization unit is positioned between the first carrier portion and the position-limiting unit, and the first position-limiting portion has an opening for exposing the micro holes.

6. A portable ultrasonic nebulizer, comprising:
a casing structure including an outer casing, a top cover rotatably disposed on a top side of the outer casing, and a nozzle disposed on an outer perimeter surface of the outer casing, wherein the outer casing has a receiving space formed on the top side thereof and covered by the top cover; and
a nebulization structure received in the outer casing and communicated between the receiving space and the nozzle, wherein the nebulization structure comprises:
a carrier unit having a first carrier portion, a first surrounding portion extended outward from an outer perimeter of the first carrier portion, a second carrier portion extended outward from an outer perimeter of the first surrounding portion, and a second surrounding portion extended outward from an outer perimeter of the second carrier portion, wherein the first carrier portion has a through hole, wherein the first surrounding portion, the second carrier portion and the second surrounding portion are sequentially connected to form a surrounding groove, wherein the first surrounding portion is extended backward and slantwise from the outer perimeter of the first carrier portion;
a vibration unit including an annular vibrating sheet received in the surrounding groove;
a waterproof package unit received in the surrounding groove to enclose the annular vibrating sheet;
a nebulization unit disposed on the first carrier portion, wherein the nebulization unit has a plurality of micro holes communicated with the through hole; and
a position-limiting unit having a first position-limiting portion disposed on the nebulization unit and a second position-limiting portion extended outward and slantwise from an outer perimeter of the first position-limiting portion and along the first surrounding portion, wherein the nebulization unit is positioned between the first carrier portion and the position-limiting unit, and the first position-limiting portion has an opening for exposing the micro holes.

7. The portable ultrasonic nebulizer of claim 6, further comprising a medicine accommodating structure, wherein the medicine accommodating structure comprises:
a medicine accommodating unit disposed in the receiving space, wherein the medicine accommodating unit includes a main body, at least one auxiliary portion adjacent to the main body, a medicine accommodating space surrounded by the main body and the at least one auxiliary portion and communicated with the receiving space, a first opening formed between one of two opposite ends of the main body and one of two opposite ends of the at least one auxiliary portion and communicated between the receiving space and the medicine accommodating space, and a second opening formed between the other end of the main body and the other end of the at least one auxiliary portion and communicated between the receiving space and the medicine accommodating space; and
a movable unit extended from an inner surface of the top cover into the receiving space, wherein the movable unit is movably disposed between the receiving space and the medicine accommodating space through the first opening;
wherein at least one pharmaceutical capsule having a medicinal liquid received therein is placed inside the medicine accommodating space, and when the movable unit is moved from the receiving space into the medicine accommodating space, the movable unit pierces into the at least one pharmaceutical capsule, such that the medicinal liquid flows from the at least one pharmaceutical capsule into the receiving space.

8. The portable ultrasonic nebulizer of claim 7, wherein the medicine accommodating unit includes a reinforcement rib connected to an outer surface of the main body, the movable unit includes a first movable element extended from the inner surface of the top cover into the receiving space and a second movable element extended from the inner surface of the top cover into the receiving space, and the first movable element and the second movable element are symmetrically disposed on the inner surface of the top cover, wherein when the top cover is rotated to concurrently move the first movable element and the second movable element, one of the first movable element and the second movable element is moved between the receiving space and the medicine accommodating space through the first opening.

9. The portable ultrasonic nebulizer of claim 6, further comprising a protection structure and a push button structure, wherein the protection structure is disposed on the casing structure, and the push button structure includes a Power push button disposed on the outer perimeter surface of the outer casing and at least one switching push button disposed on the outer perimeter surface of the outer casing, wherein the protection structure comprises:

a first protection unit including a first protection body, wherein the first protection body is disposed in front of the Power push button for covering the Power push button;

a second protection unit including two second protection bodies corresponding to each other, wherein the two second protection bodies are respectively extended backward from two opposite sides of the first protection body, and one of the two second protection bodies is disposed in front of the at least one switching push button for covering the at least one switching push button;

a third protection unit including a third protection body extended backward from a top side of the first protection body and connected between the two second protection bodies and an elastic body connected with the third protection body, wherein the third protection body is disposed on the top cover, and one portion of the elastic body is received in an exhaust vent of the top cover for enclosing the exhaust vent of the top cover; and a fourth protection unit including a fourth protection body extended forward from a front side of the first protection body, wherein the nozzle is covered by the fourth protection body for protecting the nebulization structure.

10. The portable ultrasonic nebulizer of claim 9, wherein the third protection body has a receiving hole, the receiving hole has a first receiving portion connected to an outer surface of the third protection body and a second receiving portion connected to an inner surface of the third protection body and communicated with the first receiving portion, and the width of the second receiving portion is larger than the width of the first receiving portion, wherein the elastic body has a first elastic portion received in the first receiving portion, a second elastic portion connected with the first elastic portion and received in the second receiving portion, and a third elastic portion extended downward from the second elastic portion and received in the exhaust vent of the top cover.

* * * * *